United States Patent
Piorkowski et al.

(10) Patent No.: US 11,193,090 B2
(45) Date of Patent: Dec. 7, 2021

(54) SYSTEMS AND METHODS OF FORMING AND ANALYZING DISSOLVABLE ARTICLES

(71) Applicant: Henkel IP & Holding GmbH, Duesseldorf (DE)

(72) Inventors: Daniel T. Piorkowski, Fairfield, CT (US); Joseph D. Dahlmeyer, Jr., East Haven, CT (US)

(73) Assignee: Henkel IP & Holding GmbH, Duesseldorf (DE)

( * ) Notice: Subject to any disclaimer, the term of this patent is extended or adjusted under 35 U.S.C. 154(b) by 102 days.

(21) Appl. No.: 15/980,916

(22) Filed: May 16, 2018

(65) Prior Publication Data

US 2019/0352580 A1   Nov. 21, 2019

(51) Int. Cl.
| | | |
|---|---|---|
| *C11D 11/00* | (2006.01) | |
| *C11D 3/20* | (2006.01) | |
| *C11D 3/37* | (2006.01) | |
| *C11D 3/50* | (2006.01) | |
| *G01N 21/84* | (2006.01) | |

(52) U.S. Cl.
CPC .......... *C11D 3/3707* (2013.01); *C11D 3/2093* (2013.01); *C11D 3/50* (2013.01); *C11D 3/505* (2013.01); *G01N 21/84* (2013.01)

(58) Field of Classification Search
None
See application file for complete search history.

(56) References Cited

U.S. PATENT DOCUMENTS

| | | | | |
|---|---|---|---|---|
| 5,589,099 A | * | 12/1996 | Baum | C11D 1/825 510/221 |
| 5,736,501 A | * | 4/1998 | Yamashita | C11D 1/83 264/117 |
| 8,085,987 B2 | | 12/2011 | Shalaby et al. | |
| 2005/0094853 A1 | | 5/2005 | Kang | |
| 2009/0215664 A1 | * | 8/2009 | Raehse | C11D 11/0082 510/276 |

(Continued)

FOREIGN PATENT DOCUMENTS

WO   2011056938 A1   5/2011

OTHER PUBLICATIONS

Extended EP Search Report EP 19166957.1 Completed: Aug. 16, 2019; dated Aug. 22, 2019 9 pages.

*Primary Examiner* — Lorna M Douyon
(74) *Attorney, Agent, or Firm* — Bojuan Deng

(57) ABSTRACT

Systems and methods of forming and analyzing a dissolvable article are provided herein. In an embodiment, a method of forming a dissolvable article with excellent dissolution performance includes heating a dissolvable composition that includes a water-soluble block copolymer at heating conditions that are sufficient to render the copolymer flowable and to form a hot melt composition. The water-soluble block copolymer is solid at ambient conditions. The method further includes solidifying the dissolvable composition to form the dissolvable article. A surface of the dissolvable article is analyzed for surface texture using a three-dimensional imaging device to produce a data set that is representative of the surface texture. If the data set fails to at least equal a predetermined threshold value, the method further includes reformulating the dissolvable composition to form a reformulated dissolvable composition.

11 Claims, 1 Drawing Sheet

(56) References Cited

U.S. PATENT DOCUMENTS

| | | |
|---|---|---|
| 2011/0304705 A1 | 12/2011 | Kantor et al. |
| 2012/0245074 A1* | 9/2012 | Kieffer .................. C11D 7/265 |
| | | 510/382 |
| 2015/0355101 A1 | 12/2015 | Sun |
| 2018/0044616 A1 | 2/2018 | Piorkowski |

* cited by examiner

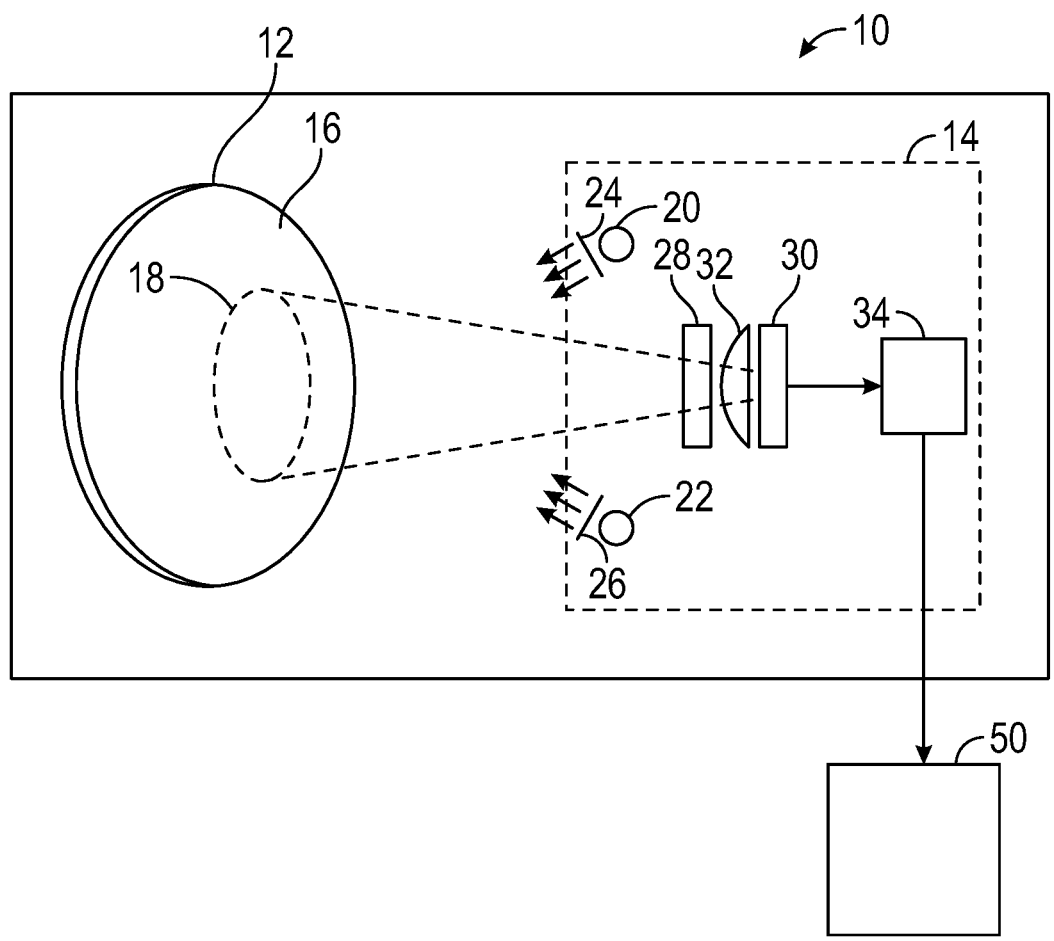

SYSTEMS AND METHODS OF FORMING AND ANALYZING DISSOLVABLE ARTICLES

TECHNICAL FIELD

The present disclosure generally relates to systems and methods of forming and analyzing dissolvable articles, and more particularly relates to systems and methods of forming and analyzing dissolvable articles to maximize dissolution performance of the dissolvable articles.

BACKGROUND

Dissolvable articles find many uses in washing applications, such as fabric laundering, dishwashing, and the like. Dissolvable articles, as described herein, refer to articles that are capable of dissolving or breaking down in water at ambient temperatures (i.e., about 21° C.) and pressures (i.e., about 101 kPa). For example, dissolvable articles as described herein are capable of breaking down in a normal wash cycle in an automatic dish or clothes washing machine, where the dissolvable article is capable of losing its original identity of form and structure in water under agitation of the water. The dissolvable articles are also generally solid and tablet-like, i.e., the dissolvable articles as described herein are not gels. The dissolvable articles deliver various components such as surfactants, fragrances, and the like. Examples of dissolvable articles include, but are not limited to, dishwashing tablets and laundry pastilles.

One type of dissolvable article that is widely employed in washing applications is formed using a water-soluble block copolymer through a hot melt process. The dissolvable articles generally include the block copolymer as a majority ingredient, but may also include other materials that factor into dissolution dynamics, such as clay fillers and acid esters. While the water-soluble block copolymer primarily provides dissolution properties to the dissolvable article, the acid ester provides the dissolvable article with increased hardness properties and renders the dissolvable article less brittle to minimize breakage prior to intended use of the dissolvable article. In this regard, the water-soluble block copolymer and the acid ester provide somewhat competing properties to the dissolvable article such that balancing of the water-soluble block copolymer and the acid ester, when present, is often desired.

To properly provide the desired effect, reliable dissolution of the dissolvable articles in the intended solvent is desired while avoiding breakage prior to intended use. While field testing involving dissolution of the dissolvable articles in the intended solvent can be conducted, such field testing may be time-consuming and cumbersome. Surface smoothness of the dissolvable articles is typically correlated to hardness/strength of the dissolvable articles, where a smoother the surface of the dissolvable article correlates with higher necessary force to break the dissolvable article (i.e., lower brittleness).

Accordingly, it is desirable to provide alternative systems and methods to objectively determine dissolution performance of the dissolvable articles. In addition, it is desirable to provide such alternative systems and methods that do not require actual dissolution of the dissolvable articles in solution. Further still, it is desirable to provide such alternative systems and methods that are capable of identifying differences in dissolution performance in solvent even when such dissolvable articles are visually indistinguishable to the naked eye. Furthermore, other desirable features and characteristics of the present disclosure will become apparent from the subsequent detailed description of the disclosure and the appended claims, taken in conjunction with the accompanying drawings and this background.

BRIEF SUMMARY

Systems and methods of forming and analyzing a dissolvable article are provided herein. In an embodiment, a method of forming a dissolvable article with excellent dissolution performance includes heating a dissolvable composition that includes a water-soluble block copolymer at heating conditions that are sufficient to render the copolymer flowable and to form a hot melt composition. The water-soluble block copolymer is solid at ambient conditions. The method further includes solidifying the dissolvable composition to form the dissolvable article. A surface of the dissolvable article is analyzed for surface texture using a three-dimensional imaging device to produce a data set that is representative of the surface texture. If the data set fails to at least equal a predetermined threshold value, the method further includes reformulating the dissolvable composition to form a reformulated dissolvable composition.

In another embodiment, a method of analyzing a dissolvable article includes providing the dissolvable article that includes a water-soluble block copolymer and a fragrance. A plurality of images of a surface of the dissolvable article are captured using a three-dimensional imaging device. The plurality of images have different spatial properties and the plurality of images are of a substantially similar viewing area of the three-dimensional imaging device.

In another embodiment, a system for analyzing dissolvable articles is provided. The system includes a dissolvable article that includes a water-soluble block copolymer, optionally a glycol fatty acid ester, and optionally a filler. The system further includes a three-dimensional imaging device, wherein the three-dimensional imaging device is configured to capture images through a photometric stereo technique.

BRIEF DESCRIPTION OF THE DRAWINGS

The present invention will hereinafter be described in conjunction with the following drawing figures, wherein like numerals denote like elements, and wherein:

FIGURE schematically illustrates a system and method for analyzing a dissolvable article in accordance with an embodiment.

DETAILED DESCRIPTION

The following detailed description is merely exemplary in nature and is not intended to limit the systems and methods of forming and analyzing dissolvable articles as described herein. Furthermore, there is no intention to be bound by any theory presented in the preceding background or the following detailed description.

The following detailed description is merely exemplary in nature and is not intended to limit the systems and methods of forming dissolvable articles as described herein. Furthermore, there is no intention to be bound by any theory presented in the preceding background or the following detailed description.

Systems and methods of forming dissolvable articles with excellent dissolution performance are provided herein. The dissolvable articles, as referred to herein, are articles that are capable of dissolving or breaking down in water at ambient temperatures (i.e., about 21° C.) and pressures (i.e., about 101 kPa). For example, dissolvable articles as described herein are capable of breaking down in a normal wash cycle, where the dissolvable article is capable of losing its original identity of form and structure in its intended solvent under agitation of the solvent, e.g., under agitation of water in a conventional dish or clothes washing machine. The systems and methods employ a three-dimensional imaging device to analyze surface texture of the dissolvable article, and the three-dimensional imaging device produces a data set that is representative of the surface texture. For example, the data set may include measurements of variables such as, but not limited to, pore density, surface roughness, elevation density, and/or depression density. Such data sets that are representative of the surface texture may be relatable to dissolution performance for the dissolvable articles. A predetermined threshold value for the data set may be established that correlates to acceptable dissolution performance for the dissolvable articles, such as by conducting testing runs by which surface texture of various dissolvable articles is analyzed with the three-dimensional imaging device in conjunction with actual dissolution of dissolvable articles in solvent. In this regard, the three-dimensional imaging devices enable an objective determination of dissolution performance to be made for subject dissolvable articles by producing the data set that is representative of the surface texture without requiring actual dissolution of the subject dissolvable articles in solution (after the predetermined threshold values have been established). Further, the three-dimensional imaging devices are capable of identifying differences in dissolution performance in solvent even when the dissolvable articles are visually indistinguishable to the naked eye. In the event that the data set fails to at least equal the predetermined threshold value, a dissolvable composition from which the dissolvable article is formed may be reformulated to form a reformulated dissolvable composition that can be subject to further analysis until the predetermined threshold value is met.

An embodiment of a system and method for analyzing a dissolvable article will now be described with reference to the FIGURE. The system 10, as referred to herein, includes devices and materials that contribute to production of a data set 50 representative of surface texture of the dissolvable article 12. In this regard, an exemplary system 10 includes a dissolvable article 12 and a three-dimensional imaging device 14, although it is to be appreciated that the system 10 may further include additional optional devices and/or materials that are employed to yield the desired data set 50.

As alluded to above, the dissolvable articles 12 as contemplated herein include any articles that are capable of dissolving or breaking down in water at ambient temperatures and pressures. The dissolvable articles 12 are also generally solid and tablet-like, i.e., the dissolvable articles 12 as described herein are not gels. The dissolvable articles 12 may be employed to deliver various components such as surfactants, fragrances, and the like to a wash composition. Specific examples of dissolvable articles 12 contemplated include dishwashing tablets and laundry pastilles, also known as solid compositions for fabric treatment (SCFTs). The SCFTs can be used, for example to treat a textile.

Water solubility can be measured by conventional methods and is a measure of dissolvability for the dissolvable articles 12. The water solubility can be measured, for example, by stir-bar method at 15° C. in 120 ppm $Ca^{2+}$/$Mg^{2+}$ water, wherein the ratio of $Ca^{2+}$:$Mg^{2+}$ is about 3:1. In one embodiment, the dissolvable articles 12 solubilize in water in about 15 minutes or less, or about 14 minutes or less, or about 13 minutes or less, or about 12 minutes or less, or about 11 minutes or less, or about 10 minutes or less, or about 9 minutes or less, or about 8 minutes or less, as measured by a stir-bar method at 15° C. in 120 ppm $Ca^{2+}$/$Mg^{2+}$ water, wherein the ratio of $Ca^{2+}$:$Mg^{2+}$ is 3:1. The term "about", as employed herein, includes the recited number ±10%. For example, "about 10" means 9 to 11.

The dissolvable articles 12 include a water-soluble block copolymer, among additional optional components as described in further detail below. The dissolvable article 12 includes the block copolymer as the predominant ingredient, i.e., as the ingredient present in a higher amount than any other ingredient, but may also include other materials that factor into dissolution dynamics, such as fillers and acid esters. While the water-soluble block copolymer primarily provides dissolution properties to the dissolvable article 12, the acid ester may provide the dissolvable article 12 with increased hardness properties and renders the dissolvable article 12 less brittle to minimize breakage prior to intended use of the dissolvable article 12. In this regard, the water-soluble block copolymer and the acid ester provide somewhat competing properties to the dissolvable article 12 such that balancing of the water-soluble block copolymer and the acid ester, when present, is often desired. The methods as contemplated herein enable an objective approach to balance components of the dissolvable articles 12 for the purposes of providing the desired properties.

In embodiments, one or more of the block copolymers of the Formulae (I) through (IV) may be included in the dissolvable article 12:

$$R^1O\text{-}(EO)x\text{—}(PO)y\text{—}R^2 \qquad \text{(Formula (I))},$$

$$R^1O\text{—}(PO)x\text{-}(EO)y\text{—}R^2 \qquad \text{(Formula (II))},$$

$$R^1O\text{-}(EO)o\text{—}(PO)p\text{-}(EO)q\text{—}R^2 \qquad \text{(Formula (III)), and}$$

$$R^1O\text{—}(PO)o\text{-}(EO)p\text{—}(PO)q\text{—}R^2 \qquad \text{(Formula (IV))},$$

wherein EO is a —$CH_2CH_2O$— group, and PO is a —$CH(CH_3)CH_2O$— group; $R^1$ and $R^2$ can independently be H or a $C_1$-$C_{22}$ alkyl group; x, y, o, p, and q can independently be 1 to about 100, provided that the sum of x and y is greater than about 35, and the sum of o, p, and q is greater than 35. In one embodiment, $R^1$ and $R^2$ are independently H. In one embodiment $R^1$ and $R^2$ are independently a $C_1$-$C_{22}$ alkyl group, a $C_1$-$C_{12}$ alkyl group, a $C_1$-$C_8$ alkyl group, or a $C_1$-$C_4$ alkyl group.

The block copolymer(s) can have, individually, a weight average molecular weight (g/mol) ranging, for example, from about 3,000 to about 12,000. Exemplary block copolymer(s) include, but are not limited to, PLURONIC®-F38 (BASF), PLURONIC®-F48 (BASF), PLURONIC®-F58 (BASF), PLURONIC®-F68 (BASF), PLURONIC®-F77 (BASF), PLURONIC®-F87 (BASF), PLURONIC®-F88 (BASF), and combinations thereof.

In embodiments, the dissolvable article 12 includes the block copolymer(s) in a total amount ranging from about 40% by weight to about 99% by weight, from about 55% by weight to about 99% by weight, or from about 60% by weight to about 90% by weight, based on the total weight of the dissolvable article 12.

As alluded to above, the dissolvable article 12 may include acid esters. Suitable acid esters include glycol fatty acid ester(s) that include a fatty acid portion having a carbon chain length ranging from about 8 carbons to about 25 carbons. In some embodiments, the glycol fatty acid ester is a monoester. In other embodiments, the glycol fatty acid ester is a diester. In some embodiments, the glycol fatty acid ester is a glycol stearate, e.g. a glycol monostearate or a glycol distearate. In some embodiments, the glycol portion of the glycol fatty acid ester has from about 1 carbon to about 8 carbons. For example, in an embodiment, the glycol portion of the glycol fatty acid ester includes only ethylene glycol. In alternative embodiments, the glycol portion of the glycol fatty acid ester includes a combination of ethylene glycol and a propylene glycol. One specific example of a suitable glycol fatty acid ester is ethylene glycol monostearate.

In embodiments, acid ester is present in the dissolvable article 12 in an amount of from about 0.05% by weight to about 25% by weight, or from about 2% by weight to about 12% by weight, based on the total weight of the dissolvable article 12. In some embodiments, the ratio of block copolymer(s) to acid ester ranges from about 75:12 to 84:1, or from about 80:7 to 83:2. It is to be appreciated that relative amounts of block copolymer to acid ester may be varied based upon the analyses conducted in accordance with the methods described herein to achieve particular dissolution performance.

As alluded to above, the dissolvable articles 12 may optionally include a filler. It is to be appreciated that in embodiments, the dissolvable article 12 does not contain a filler. In embodiments the filler is a clay. Examples of suitable clays include a smectite clay, e.g., a Bentonite clay, Beidellite clay, a Hectorite clay, a Laponite clay, a Montmorillonite clay, a Nontronite clay, a Saponite clay, a Sauconite, clay, or any combination thereof. In one embodiment, the clay is a Bentonite clay.

In other embodiments, the filler can be a starch material. The starch material can comprise starch derived from corn, potato, tapioca, cereal grain, rice, beans, peas or a combination thereof. Cereal grain includes, but is not limited to, corn, rice, wheat, barley, sorghum, millet, oats, rye, and combinations thereof.

When present, the total amount of the one or more filler(s) that can be contained in the dissolvable article 12, for example, can range from greater than 0% by weight to about 40% by weight, or from about 1% by weight to about 15% by weight, based on the total weight of the dissolvable article 12. In embodiments, a ratio of block copolymer(s) to filler ranges from about 60:30 to 85:9, or from about 80:14 to 84:10. It is to be appreciated that relative amounts of block copolymer to filler may be varied based upon the analyses conducted in accordance with the methods described herein to achieve particular dissolution performance.

In embodiments, the dissolvable articles 12 exhibit a strength of at least 5 Newtons, or at least 10 Newtons, or a range from about 5 Newtons to about 50 Newtons, or a range from about 9 Newtons to about 35 Newtons of required force to break the dissolvable articles 12 as measured using a Dr. Schleuniger Pharmatron Model 6D Tablet Tester.

The aforementioned components are typically the primary components that affect dissolution performance of the dissolvable articles 12. However, it is to be appreciated that additional components may also be present in the dissolvable articles 12 depending upon their intended use. For example, when the dissolvable article 12 is intended to be used a fragrance pastilles or SCFTs, the dissolvable article 12 includes a fragrance. Fragrance (perfume) refers to and includes any fragrant substance or mixture of substances including natural (obtained by extraction of flowers, herbs, leaves, roots, barks, wood, blossoms or plants), artificial (mixture of natural oils or oil constituents) and synthetically produced odoriferous substances. The fragrance or perfume can be an ester, an ether, an aldehyde, a ketone, an alcohol, a hydrocarbon, or a combination thereof. Further, in embodiments, at least some of the fragrance or perfume can be encapsulated, for example, in a microcapsule or a nanocapsule. In another embodiment, all of the fragrance or perfume can be encapsulated. In other embodiments, at least some of the fragrance or perfume can be free and not encapsulated. The total amount of fragrance or perfume in the dissolvable article 12 can be, for example, from about 0.1% by weight to about 25% by weight, or from about 0.1% by weight to about 15% by weight, based on the total weight of the dissolvable article 12 and such amounts include both free and encapsulated fragrance, in total.

It is to be appreciated that additional components may also be present in the dissolvable articles 12 in accordance with conventional formulary desires depending upon the intended use of the dissolvable articles 12. The additional component(s) can be, for example, a bleaching agent, a bleach activator, an enzyme, a silicone oil, an anti-redeposition agent, an optical brightener, a greying inhibitor, a shrink inhibitor, an anti-creasing agent, a color transfer inhibitor, an anti-microbial, a germicide, a fungicide, an antioxidant, an anti-static agent, an ironing aid, a water proofing agent, an impregnation agent, a swelling agent, an anti-slip agent, a UV absorber, a corrosion inhibitor, or any combination thereof. In other embodiments, the additional component(s) can be one or more viscosity-modifying agents (e.g., silica, sodium CMC, and other agents well-known in the art to increase or decrease the viscosity of a liquid or liquid-containing suspension), one or more opacifying agents, and the like. In further embodiments, the additional component(s) can be scavengers, including, for example, chlorine scavengers.

In one embodiment, the dissolvable article 12 is substantially free of polyethylene glycol, PEG fatty acid esters, PEG stearates, and/or glycerol stearates.

In accordance with an exemplary method of forming the dissolvable article 12, a dissolvable composition that includes at least the water-soluble block copolymer (optionally along with one or more or all of the ingredients in the dissolvable composition) is heated at heating conditions that are sufficient to render the copolymer flowable and to form a hot melt composition, followed by adding and/or mixing with the remaining ingredients of the dissolvable composition (if any). In embodiments, the dissolvable composition further includes the glycol fatty acid ester and, optionally, the filler along with other optional components such as the fragrance. The various components can be added in any order in accordance with conventional techniques. For example, optional components such as the glycol fatty acid ester, the fragrance, the filler, or combinations thereof may be added to the block copolymer(s) before or after the block copolymer(s) is melted. In some embodiments, the glycol fatty acid ester is melted before being added to the melted block copolymer(s). In embodiments, the water-soluble block copolymer has a melting point in a range of from about 32° C. to about 80° C. In embodiments, the dissolvable composition is aerated, i.e., air or gaseous material is incorporated or entrapped into the mixture during heating.

After heating the dissolvable composition to form the hot melt composition, the hot melt composition is solidified to form the dissolvable article 12. In particular, the hot melt composition is allowed to shape and harden. In one embodiment, the mixtures are shaped into drops, released to a surface, and allowed to cool and harden to form pastilles. In embodiments, the dissolvable article 12 is formed to have a generally flat surface 16 of sufficient area to allow effective analysis using the three-dimensional imaging device 14. For example, in embodiments, the dissolvable article 12 is formed to have a generally flat surface 16 with a surface area of at least 4 cm².

In accordance with the exemplary method, a surface 16 of the dissolvable article 12 is analyzed for surface texture using a three-dimensional imaging device 14 to produce a data set 50 that is representative of the surface texture. The data set 50 that is representative of the surface texture. For example, the data set 50 may include measurements of variables such as, but not limited to, pore density, surface roughness, elevation density, and/or depression density.

The three-dimensional imaging device 14 may be any imaging device that is capable of capturing and producing images and/or quantitative data sets 50 representing a three-dimensional shape of a surface 16 in a viewing area 18 of the imaging device 14. In accordance with the present disclosure, the three-dimensional imaging device 14 is a commercially available imaging device, and new imaging devices 14 are not contemplated by the present disclosure. Thus, while suitable three-dimensional imaging devices 14 are described herein, it is to be appreciated that various features and operation of the imaging devices 14 are endemic to the three-dimensional imaging device 14 as obtained from the manufacturer of the imaging device 14.

Various three-dimensional imaging devices 14 are known that operate through different methodologies to capture and represent the three-dimensional shape of the surface 16 in the viewing area 18. In various embodiments, the three-dimensional imaging devices 14 capture a plurality of images in such a manner that the images have different spatial properties. For example, three-dimensional imaging devices (not shown) are known that employ a "binocular stereo" technique by which a plurality of images of a substantially similar viewing area are captured by the imaging device from different viewpoints but with a static illumination angle to produce the images having different spatial properties. A depth of the surface is recovered by identifying corresponding points in the two images using software executed by a processor of the imaging device. As another example and referring to the FIGURE, three-dimensional imaging devices 14 are also known that are configured to capture images through a "photometric stereo" technique. In the photometric stereo technique, a plurality of images of a substantially similar viewing area 18 are captured by the imaging device 14 with a different illumination direction for each of the plurality of images with a constant viewing direction or viewpoint to produce the images having different spatial properties.

Referring again to the FIGURE, in embodiments, the three-dimensional imaging device 14 includes a plurality of separate illumination sources 20, 22, such as light emitting diodes (LEDs), that are positioned to illuminate the viewing area 18 of the imaging device 14 at different angles for purposes of capturing images through the photometric stereo technique. While only two illumination sources 20, 22 are shown in the FIGURE, it is to be appreciated that a number of additional illumination sources may be employed. In this embodiment, the imaging device 14 further includes an image sensor 30 and one or more lenses 32 positioned to focus images on the image sensor 30. In embodiments, the three-dimensional imaging device 14 may include an arrangement of filters 24, 26, and/or 28 that are configured to suppress specular reflection by minimizing capture of the specular reflection. For example, in embodiments and as shown in the FIGURE, the filters 24, 26, and/or 28 may be polarization filters that are positioned between the illumination source(s) 20, 22 and the surface 16 in the viewing area 18 of the imaging device 14 and/or between the image sensor 30 and the surface 16 in the viewing area 18 of the imaging device 14. The various filters 24, 26, 28 may be configured to filter electromagnetic radiation of predetermined intensity and/or wavelength prior to capturing an image of the surface 16 in the viewing area 18 using the image sensor 30. Although not shown, it is to be appreciated that the imaging device 14 may further include additional elements, such as features for shaping the illumination (e.g., light condensers and/or diffusers), additional polarization filters, imaging apertures, and other features that are conventional within three-dimensional imaging devices. In one specific embodiment, the three-dimensional imaging device 14 is an Antera 3D® camera, commercially available from Miravex of Dublin, Ireland.

As also shown in the FIGURE, the three-dimensional imaging device 14 further includes a computer processor 34 that is configured to process at least one image captured by the three-dimensional imaging device 14 using a contrast function. The contrast function is described in further detail below. An output produced using the contrast function as applied by the computer processor 34 to process the at least one image is provided by the imaging device 14.

In accordance with the exemplary method, and with continued reference to the FIGURE, a dissolvable article 12 is provided where a surface 16 of the dissolvable article 12 is analyzed for surface texture using the three-dimensional imaging device 14 to produce a data set 50 representative of the surface texture. In particular, at least one image of the surface 16 of the dissolvable article 12 is captured using the three-dimensional imaging device 14. In accordance with an exemplary embodiment, a plurality of images of a substantially similar viewing area 18 on the surface 16 of the dissolvable article 12 are captured using the three-dimensional imaging device 14, with the plurality of images having different spatial properties lending to illumination of the viewing area 18 with a different illumination direction for each of the images. By "different illumination direction", it is meant that varying levels of illumination intensity and/or illumination configurations are employed using the illumination sources 20, 22 to effectively provide different illumination conditions for each captured image. While the FIGURE illustrates illumination sources 20, 22 simultaneously emitting illumination, in practice, it is to be appreciated that only one of the illumination sources 20, 22 may emit illumination for each captured image. Alternatively, more than one illumination source 20, 22 may be illuminated for each captured image but with different illumination intensities employed for each captured image. It is to be appreciated that while only two illumination sources 20, 22 are shown in FIG. 1, numerous additional illumination sources may be employed with varying levels of illumination intensity and illumination configurations employed to provide the plurality of captured images with a different illumination direction for each of the images.

In embodiments, specular reflection from the surface 16 of the dissolvable article 12 is suppressed during analysis. For example, the specular reflection may be suppressed by one or more of polarization filtering or selective elimination of data from the data set 50 that is attributable to specular reflection. As one specific example, electromagnetic radiation of predetermined intensity and/or wavelength is filtered, e.g. using the arrangement of filters 24, 26, 28, prior to capturing the images using the image sensor 30. In embodiments, electromagnetic radiation that is attributable to specular reflection from the viewing area 18 is filtered using the arrangement of filters 24, 26, 28, with filtering conducted through conventional operation of the three-dimensional imaging device 14, such as the Antera 3D® camera.

As alluded to above, the at least one captured image is processed using a contrast function to produce a data set 50 representative of surface texture of the surface 16. As also set forth above, the three-dimensional imaging device 14 may be a commercial product. Thus, execution of the contrast function may proceed based upon programmed function from the manufacturer of the imaging device 14 with the imaging device 14 operated in a conventional manner but with images taken of the surface 16 of the dissolvable article 12 as opposed to other articles. In embodiments, the contrast function is executed by the computer processor 34 to generate a visual contrast between areas of high light absorbance of light from the illumination source(s) 20, 22 and areas of low/no absorbance of light from the illumination source(s) 20, 22. For example, in embodiments, the illumination source(s) 20, 22 emits light in a plurality of specific wavelengths that include the entire visible spectrum from UV to IR wavelengths. Radiation from the illumination source(s) 20, 22 penetrates to different depths on the surface 16 of the dissolvable article 12, with differences in measured intensity of diffuse radiation yielded based upon presence of pores, depressions, or changes in elevation on the surface 16. The computer processor 34 produces spectral curves that are based upon diffuse radiation measured at each wavelength emitted by the illumination source(s) 20, 22. The spectral curves are used to calculate tristimulus values XYZ and L*a*b* color values. This calculation may be performed for each pixel within the camera's field of view. Based upon differences between the pixels, the data set 50 may be generated. In embodiments, the data set 50 includes a measurement of at least one variable chosen from pore density (in mm3 standardized for the portion of the surface 16 in the viewing area 18 across various samples), surface roughness (in mm), elevation density (in mm3 standardized for the portion of the surface 16 in the viewing area 18 across various samples), or depression density (in mm3 standardized for the portion of the surface 16 in the viewing area 18 across various samples). Optionally, electromagnetic radiation of predetermined intensity and/or wavelength is filtered prior to generating the visual contrast. In this manner, enhanced contrast between elevation changes/pore presence in the surface 16 of the dissolvable article 12 can be achieved.

For purposes of assessing dissolution performance, the data set 50 produced using the three-dimensional imaging device 14 may be employed as an objective measure correlating surface texture to dissolution for the dissolvable articles 12. As such, the dissolvable articles 12 may be assessed for dissolution performance based upon whether or not the data set 50 fails to equal a pre-determined threshold value followed by reformulating the dissolvable composition to forma reformulated dissolvable composition if the data set 50 fails to meet the predetermined threshold value. In an embodiment, the predetermined threshold value is established for the data set 50, with the predetermined threshold value correlating to acceptable dissolution performance for the dissolvable articles 12. The predetermined threshold value may be established, for example, by conducting testing runs by which surface texture of various dissolvable articles 12 is analyzed with the three-dimensional imaging device 14 in conjunction with actual dissolution of dissolvable articles 12 in solvent to determine parameters for the data set 50 that will yield acceptable dissolution performance. Based upon the predetermined threshold values, candidate dissolvable articles 12 can later be analyzed for surface texture using the three-dimensional imaging device 14 to determine dissolution performance without actually dissolving the dissolvable articles 12. Upon failure of the data set 50 to at least equal the predetermined threshold values, the dissolvable composition may be reformulated by adjusting an amount of the water-soluble block copolymer, glycol fatty acid ester, and/or filler in the dissolvable composition to form a reformulated dissolvable composition.

The following Examples are intended to supplement the present disclosure and are not to be interpreted as limiting the subject matter as contemplated herein.

EXAMPLES

Various samples of dissolvable articles were prepared with the components and amounts thereof shown in TABLE I, where all amounts are in weight percent based upon the total weight of the composition. The dissolvable articles were formed as pastilles for laundry applications.

To form the dissolvable articles, a block copolymer (PLURONIC® F-68) was mixed with, optionally, a glycol fatty acid ester (ethylene glycol monostearate, i.e., EGMS) and the mixture was heated to about 62.7° C. until melted. A free fragrance (Azulete Neat Oil 495389) and an encapsulated fragrance (Popscent® 259366 MHN 2925 with about 30% by weight water) were added to the molten mixture. A colorant (Liquitint® Blue HP) and, optionally, a filler (bentonite) were added to the melted mixture. Mixing was effected, and the mixture was then dropped repeatedly onto a polymeric film to form drops. The drops were hardened to form pastilles, which were then removed from the polymeric film. Various dissolvable composition samples of different formulae are presented in Table I below, with all amounts in weight % based upon the total weight of the dissolvable compositions.

TABLE I

|  | SAMPLE 1 | SAMPLE 2 | SAMPLE 3 | SAMPLE 4 |
| --- | --- | --- | --- | --- |
| Block Copolymer | 84.38 | 77.68 | 64.73 | 89.99 |
| EGMS | 2.40 | 2.31 | 11.61 | 0.00 |
| Filler | 3.21 | 10.00 | 13.65 | 0.00 |
| Free Fragrance | 5.00 | 5.00 | 5.00 | 5.00 |
| Encapsulated Fragrance | 5.00 | 5.00 | 5.00 | 5.00 |
| Colorant | 0.01 | 0.01 | 0.01 | 0.01 |
| TOTAL | 100.00 | 100.00 | 100.00 | 100.00 |

The various dissolvable articles were analyzed by capturing an image of a surface of the dissolvable articles using an Antera 3D® camera, commercially available from Miravex Ltd. of Dublin, Ireland, for purposes of producing data sets that are representative of surface texture, including roughness, pore volume, depression volume, and elevation volume, with the images taken at constant distance to normalize the measurements for surface area of the surface in the image and with the samples tested at 21 C and 50% relative humidity. The data sets for the various samples are shown below in TABLE II.

TABLE II

| | SAMPLE 1 | SAMPLE 2 | SAMPLE 3 | SAMPLE 4 |
|---|---|---|---|---|
| Roughness (mm) | 3.061 | 3.848* | 4.321 | 5.458 |
| Pore volume (mm3) | 0.052 | 0.102 | 0.156 | 0.474 |
| Depression Volume (mm3) | 0.028 | 0.067 | 0.206 | 1.06 |
| Elevation Volume (mm3) | 0.292* | 0.384 | 0.933 | 1.35 |

*crack in sample; true value should be less

Physical properties of the dissolvable articles and dissolvable compositions from Samples 1-4 were determined, including melting point, strength, and water solubility. The melting point for each formulation was determined using a melting point machine (MP50 by Mettler-Toledo®). The strength of each dissolvable article was determined by measuring the force (Newtons) required to break the dissolvable articles using a Dr. Schleuniger Pharmatron Model 6D Tablet Tester. Water solubility values were determined by measuring the amount of time (minutes) required for 0.28 grams of each formulation to completely solubilize using a stir-bar method at 15° C. in 500 mL of 120 ppm $Ca^{2+}/Mg^{2+}$ water in an 800 mL beaker, wherein the ratio of $Ca^{2+}:Mg^{2+}$ is 3:1. The stir-bar method utilized a 2'×5/16' (0002) stir bar by VWR® and a standard stir plate with agitation such that the vortex is about 1 inch from the stir bar. The properties for the dissolvable articles and dissolvable compositions of Samples 1-4 are summarized in Table III below.

TABLE III

| | Melt Point Range (° C.) | Strength (N) | Solubility (Minutes) |
|---|---|---|---|
| SAMPLE 1 | 39-56 | 11.33 | 19 |
| SAMPLE 2 | 36-59 | 8.66 | 19 |
| SAMPLE 3 | 47-60 | 10.66 | 16 |
| SAMPLE 4 | 36-51 | 6 | 9 |

Based upon the results shown above, it is clear that analyzing the dissolvable articles using the three-dimensional imaging device enables fine differentiation between the various samples. Notably, while sample 4 and sample 1 were visually distinguishable based upon observation with the naked eye, the results yielded by using the three-dimensional imaging device were able to corroborate such observations. Further notable, samples 1-3 were not distinguishable by the naked eye, but the results yielded by using the three-dimensional imaging device clearly show measurable distinctions in the yielded data set that is representative of surface texture, especially the relative results for sample 1 and sample 3. The more sensitive measurements provided by using the three-dimensional imaging device may be employed to direct formulation choices.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration in any way. Rather, the foregoing detailed description will provide those skilled in the art with a convenient road map for implementing an exemplary embodiment. It being understood that various changes may be made in the function and arrangement of elements described in an exemplary embodiment without departing from the scope as set forth in the appended claims.

What is claimed is:

1. A method for formulating a dissolvable article, wherein the method comprises:
   (a) establishing a threshold value that correlates to an acceptable dissolution performance for a dissolvable article; by conducting testing runs by which surface texture of dissolvable articles is analyzed with a three-dimensional imaging device in conjunction with actual dissolution of the dissolvable articles in a solvent.
   (b) heating a dissolvable composition comprising a water-soluble block copolymer at heating conditions sufficient to render the copolymer flowable and to form a hot melt composition, wherein the water-soluble block copolymer is solid at ambient conditions;
   (c) solidifying the hot melt composition to form the dissolvable article; obtained in step (c)
   (d) analyzing a surface of the dissolvable article for surface texture comprising capturing a plurality of images of the surface of the dissolvable article using the three-dimensional imaging device to produce an observed data set representative of the surface texture including a measurement of pore density, surface roughness, and, optionally, elevation density, and depression density;
   wherein if the observed data set fails to at least equal the threshold value, the method further comprises reformulating the dissolvable composition and repeating the above steps (b) to (d) until the reformulated dissolvable composition has an observed data set at least equal the threshold value.

2. The method of claim 1, wherein heating the dissolvable composition comprises heating the dissolvable composition further comprising a glycol fatty acid ester and, optionally, a filler.

3. The method of claim 2, wherein if the data set fails to at least equal the threshold value, the reformulating comprises adjusting an amount of the water-soluble block copolymer, glycol fatty acid ester, and/or the filler in the dissolvable composition to form the reformulated dissolvable composition.

4. The method of claim 1, wherein analyzing the surface using the three-dimensional imaging device comprises suppressing specular reflection from the surface of the dissolvable article during analysis.

5. The method of claim 4, wherein suppressing specular reflection comprises one or more of polarization filtering or selective elimination of data from the data set that is attributable to specular reflection.

6. The method of claim 1 wherein analyzing the surface of the dissolvable article comprises processing the at least one image using a contrast function to produce the data set representative of the surface texture.

7. The method of claim 1, wherein heating the dissolvable composition comprises heating the dissolvable composition comprising the block copolymer and a fragrance, and wherein solidifying the hot melt composition forms the dissolvable article as a laundry pastille.

8. The method of claim 1, wherein solidifying the hot melt composition comprises solidifying the hot melt composition to form the dissolvable article having a flat surface of sufficient area to allow effective analysis using the three-dimensional imaging device.

9. The method of claim 8, wherein solidifying the hot melt composition comprises solidifying the hot melt composition to form the dissolvable article having a flat surface with a surface area of at least 4 $cm^2$.

10. The method of claim 1, wherein analyzing the surface of the dissolvable article for surface texture comprises using the three-dimensional imaging device to produce the observed data set representative of the surface texture further including a measurement of elevation density.

11. The method of claim 1, wherein analyzing the surface of the dissolvable article for surface texture comprises using the three-dimensional imaging device to produce the observed data set representative of the surface texture further including a measurement of depression density.

\* \* \* \* \*